United States Patent [19]

Rotariu et al.

[11] Patent Number: 4,971,049

[45] Date of Patent: Nov. 20, 1990

[54] PRESSURE SENSOR CONTROL DEVICE FOR SUPPLYING OXYGEN

[75] Inventors: William J. Rotariu, Port St. Lucie, Fla.; Darold Wobschall, Williamsville, N.Y.

[73] Assignee: Pulsair, Inc., Fort Pierce, Fla.

[21] Appl. No.: 432,067

[22] Filed: Nov. 6, 1989

[51] Int. Cl.$^5$ ............................................. A61M 16/00
[52] U.S. Cl. ........................... 128/204.21; 128/204.26
[58] Field of Search ....................... 128/204.18, 204.21, 128/204.23, 204.26

[56] References Cited

U.S. PATENT DOCUMENTS

| | | | |
|---|---|---|---|
| 3,741,208 | 6/1973 | Jonsson et al. | 128/204.21 |
| 3,952,739 | 4/1976 | Cibulka | 128/204.23 |
| 3,961,627 | 6/1976 | Ernst et al. | 128/204.21 |
| 3,972,327 | 8/1976 | Ernst et al. | 128/204.21 |
| 4,462,398 | 7/1984 | Durkan et al. | 128/204.23 |
| 4,584,996 | 4/1986 | Blum | 128/204.21 |
| 4,612,928 | 9/1986 | Tiep et al. | 128/204.23 |
| 4,617,637 | 10/1986 | Chu et al. | 128/204.21 |

*Primary Examiner*—Edgar S. Burr
*Assistant Examiner*—Aaron J. Lewis
*Attorney, Agent, or Firm*—Larson and Taylor

[57] ABSTRACT

A flow control device for supplying oxygen to a medical patient using provides pulses of oxygen only when the patient inhales, using a flow valve unit that receives a pressurized oxygen supply and delivers a controlled oxygen supply output through a cannula to a patient. A pressure sensor detects breathing changes and output signals that are amplified and automatically corrected for signal errors, such as those caused by offset voltage and temperature drift, by use of a negative integral feedback module that includes automatic correction circuits and a switch for selectively disconnecting the feedback. The amplified sensor signal generates control signals, including an output pulse delivered to the flow valve, having a pulse width that is a user adjustable for control of the opening and closing of a valve, such as a three-way solenoid valve, for outputting time selectable pulses of oxygen to the patient when patient inhalation is detected by the pressure sensor.

31 Claims, 8 Drawing Sheets

PRESSURE SENSOR CONTROL DEVICE FOR SUPPLYING OXYGEN

FIELD OF THE INVENTION

The present invention relates generally to devices for flow control in supplying supplemental oxygen to a medical patient, and more specifically, to a device that delivers a controlled flow of oxygen only upon inhalation by a patient with automatic correction applied to sensor signals for actuation of flow control means to produce a precisely timed oxygen supply.

BACKGROUND OF THE INVENTION

In the medical field, patients frequently require supplemental oxygen due, for example, to a diminished lung function caused by a disease or disorder. Continuous flow devices are known that provide a supply of such supplemental oxygen to a patient. However, there are undesirable effects of such devices, such as an inefficient use of the oxygen supply since the oxygen is not needed continuously, and this results in increased medical costs to the patient.

It is known to use pressure sensors in connection with devices that provide automatic delivery of oxygen for medical purposes. However, the electronic signals produced by such pressure sensors, and this even includes those having built-in temperature compensation, often exhibit too much drift to enable use of the sensor in providing a precise, timed delivery of oxygen. In this regard, the signal drift occurring in pressure sensors commonly used in supplying medical oxygen, which is typically between 0.05% and 2%, can be significant relative to a 1 PSI full-scale measurement range provided by such sensors. Although more sensitive pressure sensors for such medical applications are currently available, such sensors are fragile and thus easily damaged, and are relatively costly as well.

Thus, a need exists in the industry for a device that accurately provides supplemental oxygen to a patient only when the oxygen is needed, i.e., at the time the patent inhales, without the drawbacks found in controlled devices that are now available, and particularly without the adverse effects caused by signal drift associated with the pressure sensor used to detect patient inhalation and activate the flow control system. Such a device should also be portable and include automatic built-in correction for temperature drift and signal offset present in the signal processing circuitry to accurately delivery the supplemental oxygen. While supplemental oxygen control devices of the types known in the art are satisfactory for many applications, they do not meet the above-identified needs, nor do they in general provide the various advantages present in the invention as described below.

SUMMARY OF THE INVENTION

In accordance with the invention, a pressure sensor control device is provided that controls a valve which releases oxygen to an individual requiring supplemental oxygen. A pressure sensor detects inhalation, outputs a sensor signal that is amplified and corrected for signal errors, such as those caused by voltage offset and temperature drift, and the corrected sensor signal is processed by a control signal generation circuit, which comprises timer circuits, to produce control signals delivered to an input terminal of a flow control means. The flow control means can, for example, be a solenoid valve, such as a 3-way solenoid valve, that is turned on and off for predetermined periods of time in controlling the oxygen flow.

The device basically comprises a pneumatic control unit and an electronic control unit. The pneumatic control comprises a flow valve controller that receives a pressure regulated source of oxygen and delivers a controlled oxygen output to a patient. The delivery, for example, could be through a nasal cannula or a transtracheal catheter, or by using other suitable delivery means. The flow controller could comprise a solenoid valve having an orifice at its oxygen supply input, with the valve being opened and closed by electronic control signals.

Within the electronic control unit, electronic signals are generated and outputted to activate the valve to permit oxygen to flow. The volume of oxygen delivered per pulse dose is controlled by the flow rate through the orifice and the on-off times of the valve. The cannula, in addition to providing the conduit through which oxygen is delivered to a patient, is also connected to a pressure sensor in the electronic control unit which detects inhalation by the patient. When inhalation is sensed, signals are produced, processed and outputted to control the operation of the solenoid valve and thus regulate the oxygen flow.

The electronic control unit preferably comprises a silicon diaphragm pressure sensor. Inhalation by the patient causes a decrease in pressure in the cannula which is detected by the pressure sensor and the sensor outputs a signal as a function of the detected pressure. The pressure sensor signal is amplified to produce an output signal that is inputted to a comparator, which compares the sensor signal to a threshold signal level. When the threshold is exceeded, at least one timing pulse is generated as output from the control device which turns on the solenoid valve for a selected time interval to allow oxygen to flow to the patient.

Automatic correction circuits for both the pressure sensor and its associated signal amplifier compensate for both signal offset and signal temperature drift to provide a precise, timed output signal and an improved control of the oxygen delivery. The automatic correction circuits, together with a negative feedback integrator having a long time constant, are included in a feedback loop from the output of the amplifier. When the solenoid valve is open and oxygen flows to the patient this causes a large positive pressure pulse at the output of the pressure sensor which normally would adversely affect the correction benefits of the negative integral feedback. However, the feedback loop is automatically disconnected when the solenoid valve is open and oxygen flows and for a predetermined time thereafter. Otherwise, the correction circuit is connected in the electronic control unit when the valve is off, i.e., unit when the valve is off, i.e., oxygen is not flowing, and automatically provides signal correction that avoids erroneous readings and offers more accurate device operation. In the operation of the automatic correction circuit, the average value of the cannula pressure is assumed to be zero, and automatic corrections are made for small deviations that might occur from this average zero pressure.

The control device, including both its sensor and processing circuits, could be powered by a rechargeable 6-volt battery, which would then constitute a compact and portable means for delivering a regulated and precise timed supply of supplemental oxygen.

Other features and advantages of the invention will be set forth in, or apparent from, the detailed description of the preferred embodiments of the invention which follows.

BRIEF DESCRIPTION OF THE DRAWINGS

For a complete understanding of the objectives and structure of the invention, reference is made to the following detailed description and accompanying drawings, wherein.

DETAILED DESCRIPTION OF THE PREFERRED EMBODIMENTS

Figure 1:
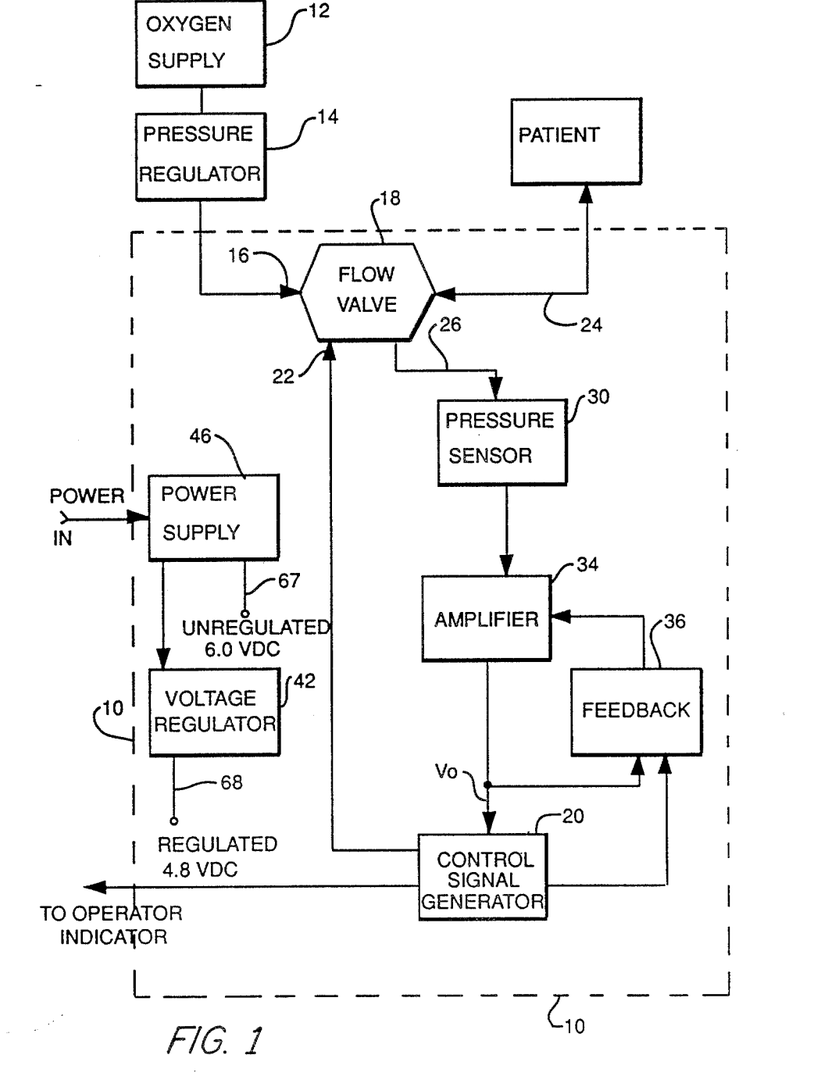
FIG. 1 shows a block diagram of the oxygen control device according to the invention.

FIG. 1 shows a block diagram of a flow control system 10 for supplying oxygen, constructed according to a preferred embodiment of the invention. Oxygen from an oxygen supply 12 such as a pressurized tank of oxygen, is regulated by pressure regulator 14 and is inputted to flow control system 10. In particular, oxygen is supplied to an input port (valve orifice) 16 of a flow control or flow valve unit 18 which, in the preferred embodiment, is a 3-way solenoid valve. Valve orifice 16 controls the volume of oxygen flow into flow valve 18. Solenoid flow valve 18 is electronically opened and closed by pulse signals outputted from a control signal generation unit 20 and received by flow valve 18 at valve input terminal 22. An output line (cannula) 24 from the solenoid valve delivers a controlled oxygen flow to a medical patient in a first state of valve 18. In a second state of valve 18, output line 24 is connected as an input to a pressure sensor 30 through, for example, transfer ports in flow valve 18, as it monitors the breathing of the patient, and more specifically, solenoid valve 18 in its second state connects line 24 to pressure sensor 30 which detects pressure changes occurring based upon the breathing of the patient.

Figure 3:
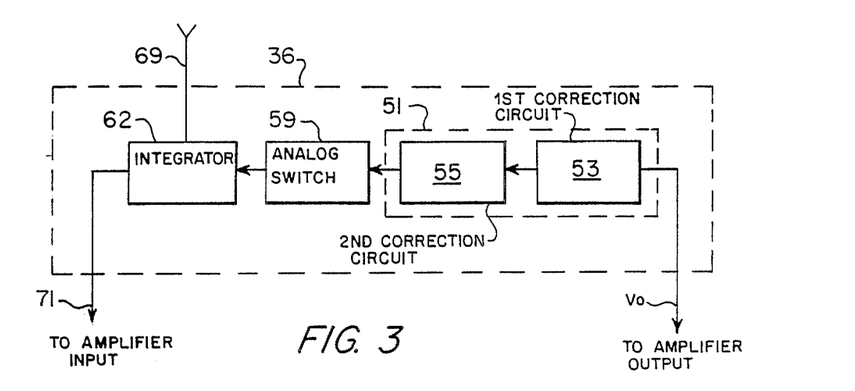
FIG. 3 shows a block diagram of the feedback module.

The pressure sensor 30 is connected through an amplifier 34. The output of amplifier 34 is connected to a feedback module 35, whereby the feedback signal is integrated and provided with automatic correction as it proceeds through the various circuits of the feedback loop. Feedback module 36 is shown in block diagram form in FIG. 3.

The corrected, amplified sensor signals are received by control signal generation unit 20, from which control signals are generated and inputted to flow valve 18 to control the oxygen flow through flow valve 18. The control signal generation unit also provides output signals for operator indicators, such as audio and/or visual alarms, as well as producing signals to feedback circuit 36, and controlling operation of various timer circuit modules.

A power supply to the flow control system provides both a regulated and an unregulated DC voltage output for powering the various components of the system.

The individual units or circuits of the flow control system will be described separately below.

Pressure Sensor 30

Figure 4:
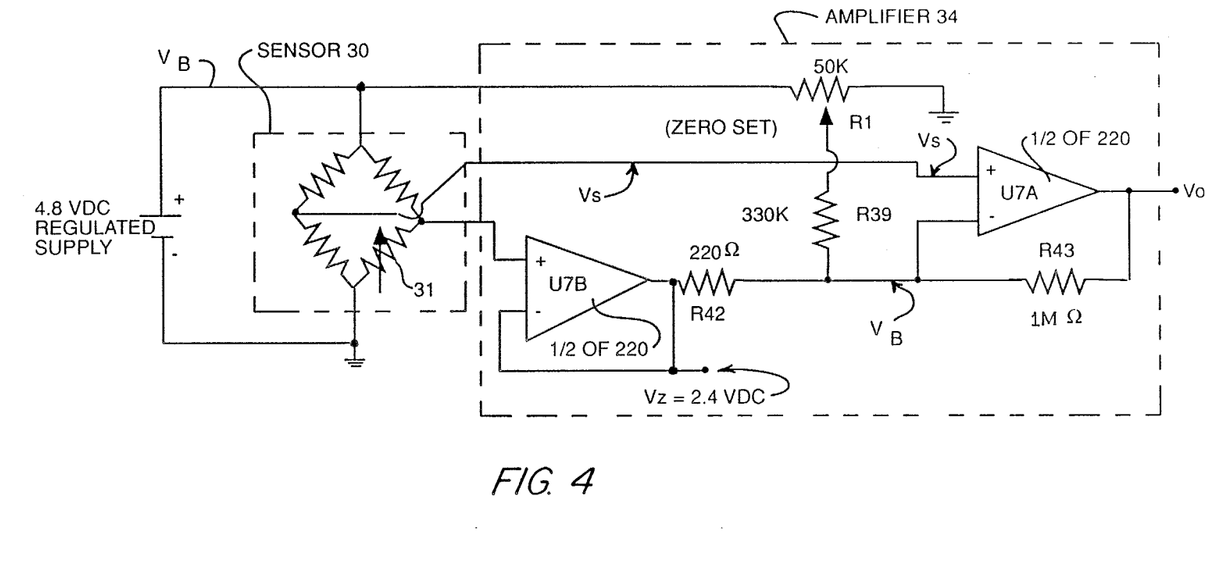
FIG. 4 shows circuitry of the pressure sensor and amplifier.

As mentioned above, pressure sensor 30 is connected to output port 26 of flow valve (or solenoid valve) 18, and serves to sense or detect changes in a patient's breathing, e.g., inhalation and exhalation. Changes in pressure due to changes in breathing result in a characteristic output signal from the pressure sensor 30, as described in more detail below. Pressure sensor 30 includes built-in temperature compensation circuitry in order to enable the correction circuits of the invention to operate effectively. Such pressure sensors are commercially available. A Sensyn model SCX01DNC pressure sensor is used in the preferred embodiment. Electrically, this sensor is equivalent to a 4 Kohm strain gage resistance bridge which is unbalanced by the pressure on the silicon diaphragm of the sensor 30. FIG. 4 schematically shows sensor 30 as its equivalent bridge circuit, connected to the amplifier circuit 34.

Sensor 30 is powered by a regulated supply voltage of 4.8 volts, which provides a 1 PSI full-scale output of 7.2 mV at 1.5 mV per volt of excitation, with a zero offset of 0.1 mV/volt. This particular sensor specifies an initial zero offset of 0.4 mv and a shift up to 0.4 mv with temperature and age. The sensor has internal temperature compensation rated at 0.03 mv/volt maximum (0° to 70° C.). Inhalation causes a decrease in pressure at the input of pressure sensor 30 which produces a sensor output negative pulse. A typical input signal of 0.005 PSI generates a sensor output signal of (only) 0.018 mv. A pulse amplitude range of 0.01 to 0.10 mv can be expected, which is smaller than the rated temperature drift of the sensor. However the minimum noise level which characterizes the sensor allows the inhalation pulse generated to be easily detected. A nominal pulse amplitude of 0.03 mv is assumed for the analysis that appears later herein.

Other silicon diaphragm pressure sensors with higher sensitivities, e.g., 5 inches of water (0.18 PSI) full-scale, are generally unsuitable because the peak pressures which occur when the solenoid valve operates may exceed the maximum operating pressure of the sensor. Also, sensors without temperature compensation are unsuitable because they generally show too rapid a signal variation with temperature change, thus preventing effective operation of the automatic zero circuit of the invention.

Amplifier 34

Amplifier 34 (FIG. 1) provides amplification of the small signal output of the 4 kohm (typical) resistance bridge circuit (FIG. 4) of pressure sensor 30, where variable resistor 31 represents the variable diaphragm of the sensor, to a level that can be handled easily by subsequent signal processing circuitry of the invention. Amplifier 34 is a high gain, low noise, low drift amplifier. In the preferred embodiment, a commercially available OP220 dual amplifier is used, which is shown as amplifiers U7A and U7B in FIG. 4.

As shown in FIG. 4, one side of the sensor bridge outputs a sensor signal $V_s$ to the positive input terminal of main amplifier U7A. The other side of the sensor bridge is connected to the positive input terminal of unity gain buffer amplifier U7B, which produces a zero reference signal, $V_z$. The buffer amplifier U7B is used to overcome temperature variation associated with the high sensor resistance.

The amplifier low-frequency noise, which must be low for effective operation of the correction circuits of the invention, is rated at 700 mV/$\sqrt{Hz}$ at its input, which corresponds to about 3mV at its output ($V_o$). Generally, 3 to 10 mV (peak) low frequency noise can be expected for the OP220 shown, which is considerably better than many other op-amps having output noise levels 5-10 times higher. Use of the OP220 op-amp is also favored because it has a low supply current to conserve battery life in portable use operation.

The pressure sensor output signal ($V_s$) applied to the positive input of amplifier U7A is done so with respect to the zero reference ($V_z$) provided by amplifier U7B appearing at the negative input terminal of amplifier U7A. The signal gain of amplifier U7A is determined by the ratio of the values of the resistances R43 and R42, in this case being 1,000/0.220, for a gain of about 4500. Thus, a typical amplified sensor signal out, $V_o$, is equal to $(V_s-V_z)$, or $(0.018-0)=0.018 \times 4500 = 81\ m/V$.

Both the sensor offset (0.12 mV max.) and the amplifier offset voltage, as well as temperature drift error, are compensated for by the automatic correction circuits of the invention. A 0.5 mV offset is typical for the pressure sensor/operational amplifier combination (SCX01DNC/OP220) used in the preferred embodiment. A compensation voltage adjustment, $V_b$, is provided for by potentiometer R1 in FIG. 4, where the maximum compensation setting is determined by the ratio R42/R39, typically being $\pm 1.6$ mV.

Feedback Module 36

Figure 5:
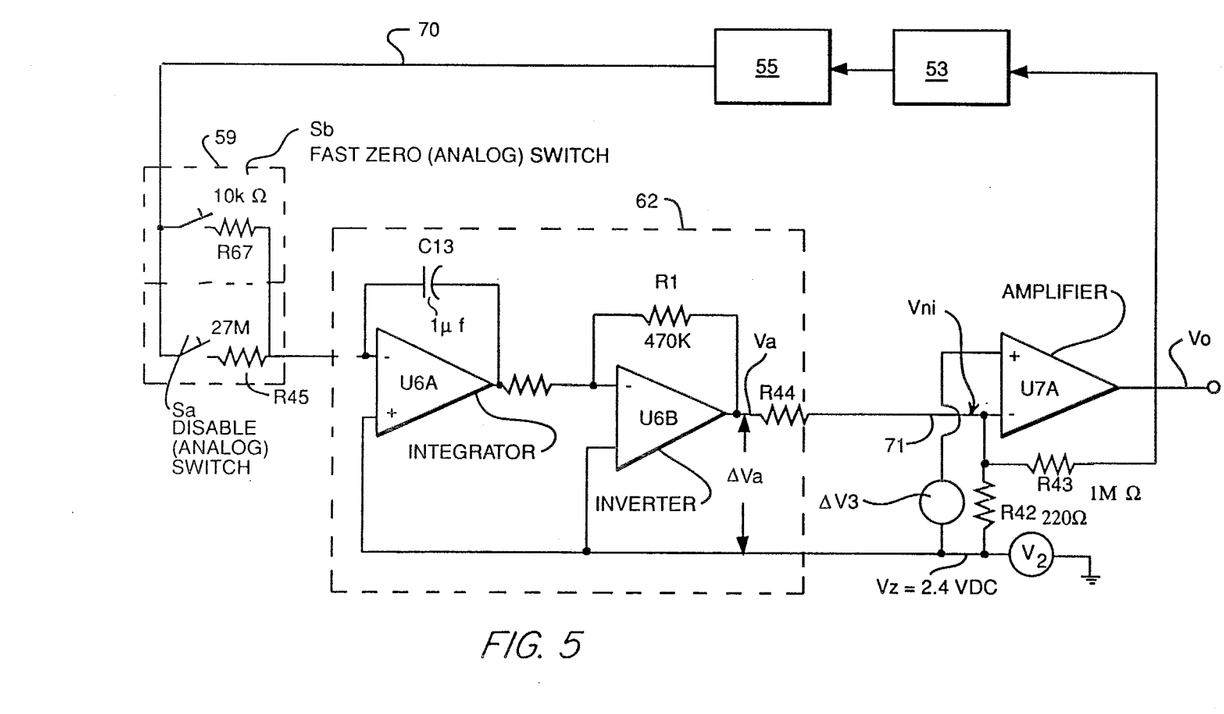
FIG. 5 shows circuitry of components of the feedback module in relation to the amplifier circuit receiving the sensor output signal.

A part of the feedback module 36 of FIG. 1 is shown in more detail in FIG. 5, in combination with a simplified representation of the amplifier 34 of FIG. 4. Module 36 receives as an input the output amplified sensor signal, $V_o$, from amplifier U7A. An integrator circuit within the feedback module (FIG. 3) adjusts the average value of output signal $V_o$ to zero by integrating any difference voltage by means of an integrator U6A, as shown in FIG. 5. The 1 μfd feedback capacitor C13 with a 27 Megohm input resistor R45 produces a 27 second (long) time constant. With this length time constant, the integrator does not respond to small, brief inhalation pulses which have rise times less than 1 second (typically 0.05 seconds), and thus represent undesired signals. Since most breath cycles (inhalation plus exhalation) take 2 to 5 seconds, this 27 second time constant allows an average to be made over several breath cycles. Long-term signal changes, e.g., due to temperature, are thus also corrected by this integrator correction circuit.

The output of integrator U6A is inputted to an inverter circuit U6B to produce negative feedback, and is then fed back to the input of amplifier U7A to correct for offset voltage. This circuit provides an accurate, long term zero of signal $V_o$ where signal offset under 10 mV is achieved. This type of feedback control is commonly termed "integral feedback".

The "zeroing" signal, $\Delta V_a = V_a - V_z$, is inputted to main amplifier U7A through R44 (FIG. 4). The zero correction voltage $\Delta V_a$ is inputted to the inverting input of U7A which is set for a gain of two. The input voltage, $V_{in}$, to amplifier U7A is:

$$V_{in} = V_a(R44/R42)$$

The output $V_o$ of the amplifier is:

$$V_o = -\Delta V_a(R44/R43) = -2\ \Delta V_a$$

As noted above, the zero correction voltage is derived from the amplifier output voltage, $V_o$. As shown in FIG. 5, a feedback circuit connected between the output of amplifier U7A and integrator U6A includes a disable switch $S_a$ and a fast zero switch $S_b$ connected in parallel. With disable (analog) switch $S_a$ closed, i.e., with the feedback circuit not disabled, and switch $S_b$ open, i.e., with the feedback circuit not in its fast zero mode, the signal $V_o$ is applied as an input to integrator U6A through resistor R45 (27 Megohm). Because of the long integrator time constant of Integrator 62, integrator circuit U6A responds only to the average $V_o$ signal. After signal inversion at unity gain provided by inverter U6B, the output $\Delta V_a$ can be expressed as:

$$\Delta V_a = 1/R_1 C_1 \int \Delta V_o dt$$

Figure 6A:
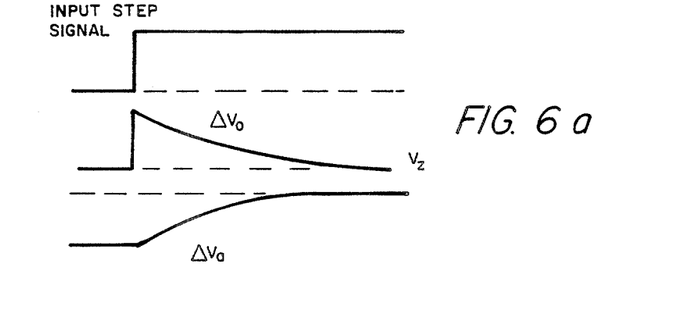
FIG. 6(a) shows an input step signal and the output response of the automatic zeroing circuit of the invention.
Figure 6B:
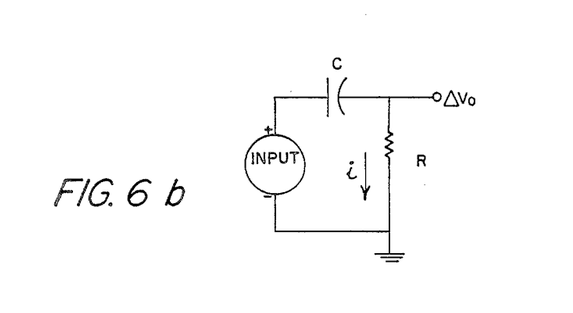
FIG. 6(b) shows the equivalent high pass filter circuit of the step signal response of FIG. 6(a).

FIG. 6 shows the response of the zeroing circuit to a unit step signal input, e.g., 100 mV. The decay is exponential (similar to a simple RC decay), with the long time constant of $$\frac{(R45)(C13)}{A_c} = 27\ \text{seconds.}$$

Since most breath cycles (inhalation plus exhalation) take 2 to 5 seconds, this 27 second time constant allows an average to be made over several breath cycles. Long-term changes, e.g. due to temperature, are thus corrected by the automatic zero circuit.

Referring to FIG. 6, if $\Delta V_o$ is positive, $\Delta V_a$ will slowly rise. But as $\Delta V_a$ becomes more positive, more negative signal is inputted into the main amplifier, thus making $\Delta V_s$ less positive and thereby reducing the zero offset and signal average ($V_o$). As long as $\Delta V_o$ is positive, the output ($V_a$) of integrator U6B will continue to rise, but if $\Delta V_o$ becomes negative, $\Delta V_a$ will fall (ramp negative). The connecting output signal from inverter U6B, $\Delta V_a$ will be zero only when the DC average of signal $\Delta V_s$ is zero.

Feedback circuit 36 of FIG. 1 also comprises a Disable and Fast Zero circuit for use in disconnecting the automatic zero circuit at predetermined times. This is comprised within analog switch 59 of FIG. 3, which is further shown as switch $S_a$ and switch $S_b$ in 59 of FIG. 5.

The feedback is disconnected at preselected times during the operation of the flow control device due to the nature of the sensor signals generated. When oxygen solenoid valve 18 is turned on, a large positive pressure pulse is produced at the input of pressure sensor 30. This pulse is at least ten times larger and lasts much longer than the negative inhalation pulse. If this pulse were allowed to appear at the input of integrator circuit U6A (FIG. 4), it would shift the zero voltage positive, thus moving the threshold to an unpredictable level. To prevent this, the feedback integrator U6A is disconnected when the valve 18 is "On", and for a period (approx. 0.5 sec.) thereafter. The disabling of the integrator U6A is accomplished by disable (analog) switch $S_a$ which is activated when the valve-on signal occurs. Although two series switches are actually used in order to reduce leakage, only a single switch $S_a$ is shown in FIG. 5. The size of off-scale (erroneous) signals into the integrator U6A are also limited by the gain of amplifier U7A which is made very high so that op-amp saturation occurs with a relatively small signal.

When valve 18 is in an "Off" condition (i.e., the valve-on signal from timer unit 20 is, as discussed below, LOW), no oxygen flows through valve 18, switch $S_a$ is closed, and signal $V_o$, connected from the output of amplifier U7A to switch $S_a$, is inputted to integrator U6A. When the valve is "On", i.e., oxygen flows, switch $S_a$ is open and any signal leakage through a first switch device within switch $S_a$ is bypassed through a 1 Mohm resistor (not shown) to $V_z$ (signal common).

The turn-on time of one of the two switches comprising switch $S_a$ is delayed by about 500 ms due to the fact that the pressure sensor signal has a decay time of 50–300 ms. The 500 ms delay is accomplished by a time constant produced by a conventional capacitor-resistor network, with a diode providing a rapid discharge and thus turn-off of the switch.

Immediately after power-up, a switched in R-C network (not shown) closes switch $S_b$ and reduces the time constant to about 27 ms. This allows the signal to be completely zeroed quickly (within a 200 ms interval) when power is turned on.

Included in feedback module 36 (FIG. 1) are also first correction circuit 53 and second correction circuit 55, together referred to as correction means 51 (FIG. 6).

Figure 7:
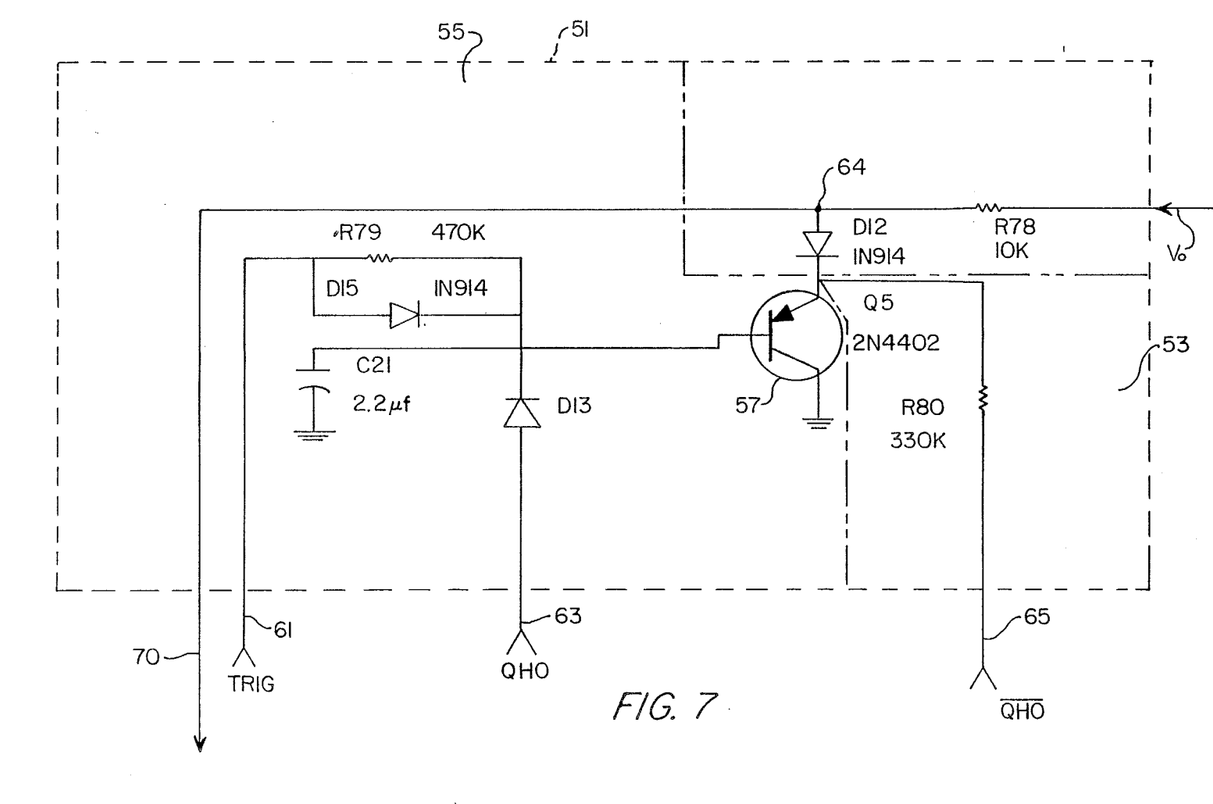
FIG. 7 shows circuitry of the first and second correction circuits.
Figure 8A:
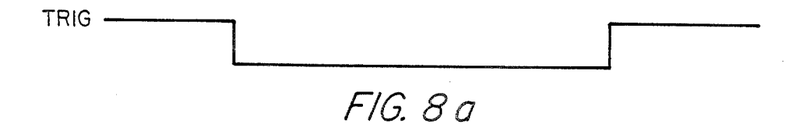
FIG. 8a, 8b, 8c, 8d, and 8e show the timing relationship between various signals in the oxygen control device.
Figure 8B:
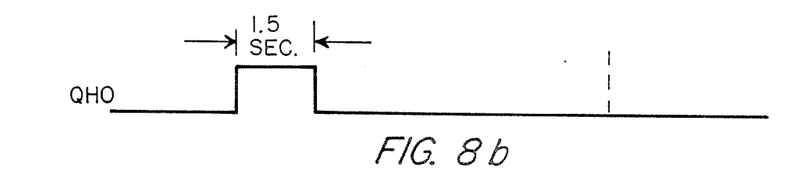
Figure 8C:
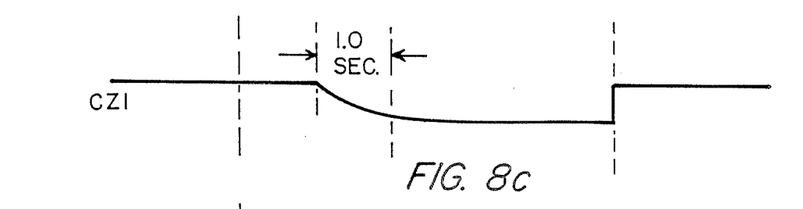
Figure 8D:
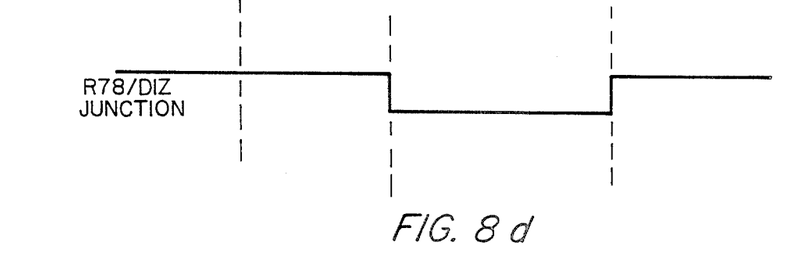
Figure 8E:
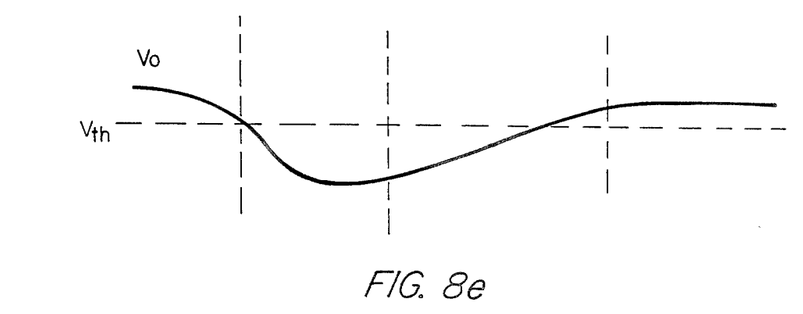
Figure 9A:
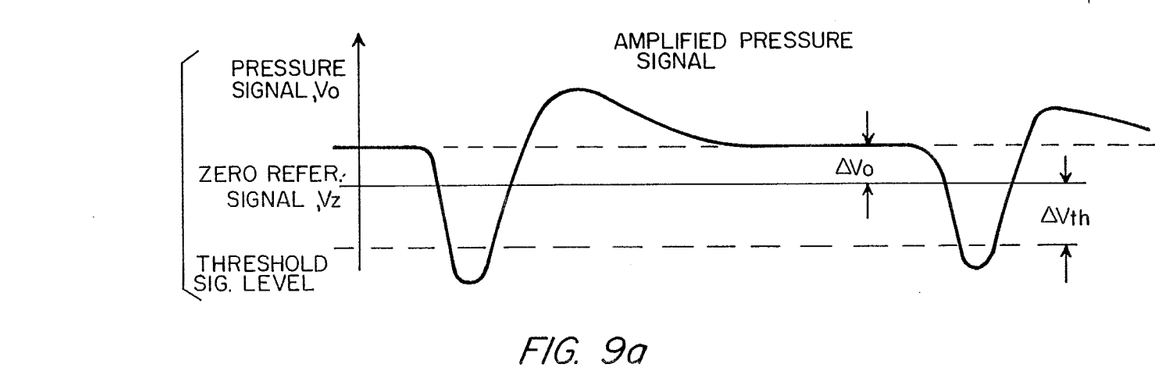
FIG. 9a and 9b show the timing relationship between an amplified sensor signal, zero reference and threshold signals, and comparator trigger signal.
Figure 9B:
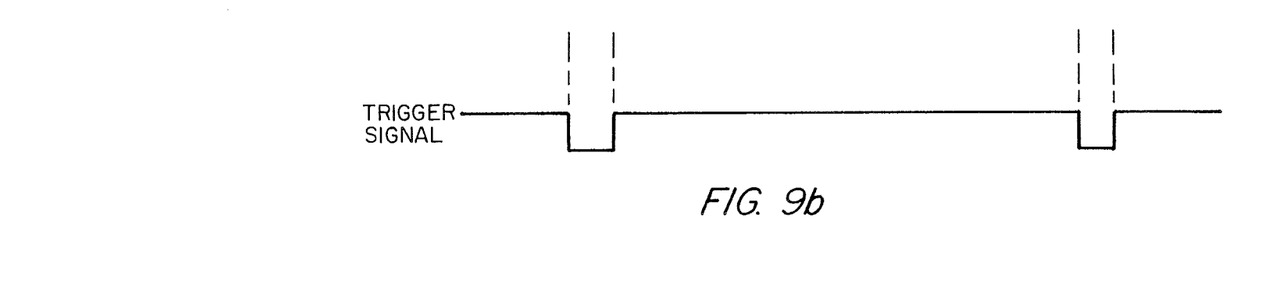

FIG. 7 shows the circuit schematic of correction circuit 51 that comprises first correction circuit 53 and second correction circuit 55. Correction circuit 51 is connected in series with analog switch 59 and integrator 62 which are included within feedback module 36. It is noted that the dotted/dash line that divides 53 and 55 does not separate diode D12 and resistor R78 because D12 and R78 are common to both correction circuits.

With respect to correction circuit 51, when second correction circuit 55 is not activated, transistor switch 57 remains off (circuit 53 does not use transistor 57), and the feedback signal starting at $V_o$ is connected through resistor R78, to output terminal 70 of correction circuit 51. Beyond correction circuit 51, the feedback signal passes through analog switch 59, to integrator 62 (FIG. 3) which produces a negative integral feedback signal at output terminal 71 of the feedback loop, and is connected to the negative input terminal of amplifier U7A (FIG. 5).

First correction circuit 53 is activated upon receipt of a signal $\overline{QHO}$ from hold-off timer 21, which outputs a hold-off timer pulse, having an appropriate 1.5 second pulse width, designated as signal QHO. At the same time, hold-off timer 21 also outputs an inverted QHO pulse, designated $\overline{QHO}$. It is this inverted pulse, $\overline{QHO}$, that is provided as input at terminal 65 to activate first correction circuit 53 for the duration of the pulse. The effect of signal $\overline{QHO}$ is to produce a voltage drop at terminal 64 which provides the correction of first correction circuit 53 to output signal $V_o$.

Second correction circuit 55 is activated by the presence of an AND condition; specifically, when the output of comparator 38 is LOW and hold-off timer 21 finishes timing out, i.e. at the end of its 1.5 second output pulse. If both of these AND conditions are met, i.e. occur at the same time, then transistor 57 is activated by receipt of comparator 38's output trigger signal at TRIG input 61, and receipt of the hold-off timer output pulse QHO at terminal 63 of second correction circuit 55. This also causes a voltage drop at junction 64 in the feedback loop, different from that produced by the first correction circuit, and the corrected feed back signal is outputted from correction circuit means 51 at its output terminal 70.

Capacitor C21 in second correction circuit 55 causes a slight delay, i.e. provides a slight buffer, before the AND condition activates the second correction circuit. So long as the two above-described conditions exist, i.e. until the comparator trigger output goes HIGH again, second correction circuit 55 stays activated in providing automatic correction to the output signal $V_o$ of amplifier 34.

FIG. 8 illustrates a time relationship between various signals with respect to the functioning of second correction circuit 55. The signal of FIG. 8(a) represents the trigger signal at the output of comparator 38; graph 8(b) represents the 1.5 second output pulse from hold-off timer 21, QHO; graph 8(c) represents the discharge of capacitor C21 through resistor R79 in providing a slight delay to the activation of the second correction circuit, with capacitor C21 of the second correction circuit being charged through diodes D15 or D13; graph 8(d) shows the voltage change at junction 64 from an initial voltage level to that produced by second correction circuit 55; and graph 8(e) shows the relationship between the threshold voltage level $V_{th}$ of comparator 38 and the amplified pressure sensor signal $V_o$ outputted from amplifier 34. From FIG. 8, it is seen that as pressure sensor output signal $V_o$ drops below reference level $V_{th}$, an output negative trigger generated by comparator 38 produces a 1.5 second pulse signal QHO outputted from hold-off timer 21. After a slight delay, a discharge of capacitor C21 in second correction circuit 55 produces a second correction voltage change at junction 64 to provide automatic correction to $V_o$ by means of feedback circuit 36.

Control Signal Generator 20

Control signal generator module 20 includes a comparator circuit and various timer circuits. The timer circuits comprise a hold-off timer 21, a valve-on timer 23, and a power-up timer 25.

Comparator 38

Any differences between the amplified sensor output signal, $V_o$, and a threshold voltage $V_{th}$, is detected or measured by comparator circuit 38 which receives as inputs both the sensor signal $V_o$ and a variable threshold signal, $V_{th}$. Such comparator circuits are commercially available and, in the preferred embodiment, one half of the low power operational amplifier IC7621 integrated circuit is used.

In operation, a change in output signal voltage from amplifier 34, $\Delta V_o = V_o - V_z$, is compared by comparator 38 to a change in threshold voltage, $\Delta V_{th} = V_{th} - V_z$ (FIG. 5). When there is no inhalation by the patient, no signal $V_o$ is generated and the output of the comparator circuit 38 is HIGH. When inhalation occurs, a negative signal is produced that exceeds the $\Delta V_{th}$ threshold voltage of the comparator 38, causing the comparator output to go LOW, thereby producing a comparator output trigger pulse (FIG. 8(a)). This trigger pulse, in turn, triggers a hold-off timer circuit, which then triggers a valve-on timer circuit, discussed below. These circuits are part of control signal generator 20. Oscillation at the edge of the trigger pulse is minimized by means of a positive feedback resistor (not shown) used to produce a small amount of hysteresis. In the preferred embodiment, hysteresis in the amount of 1 mv is used to minimize oscillation at the comparator output.

It is also noted that high frequency noise pulses originating from external sources at the comparator input can cause undesired triggering of the comparator 38 at the wrong time. This can be avoided by use of a capacitor (not shown) in combination with a resistor (not shown) to serve as a low pass filter to remove such high frequency input noise pulses.

The threshold voltage $V_{th}$ inputted to one input terminal of comparator 38 is obtained by a resistance voltage divider containing a potentiometer (not shown). As the potentiometer is adjusted, the resistance varies and so does the threshold range.

Hold-Off Timer 21

The hold-off timer 21 receives the output trigger pulse of comparator 38 and produces an output pulse which, in the preferred embodiment, has a pulse width of 1.5 seconds, which is considered to be the minimum time interval between solenoid valve operation, i.e., between oxygen pulse deliveries. A resistor-capacitor circuit (not shown) is used to establish the selected 1.5 second pulse width. The hold-off timer is of a non-retriggerable configuration, so that all other input trigger pulses to the hold-off timer, e.g., other inhalations, occurring within the 1.5 second pulse width time interval, are ignored.

Figure 2:
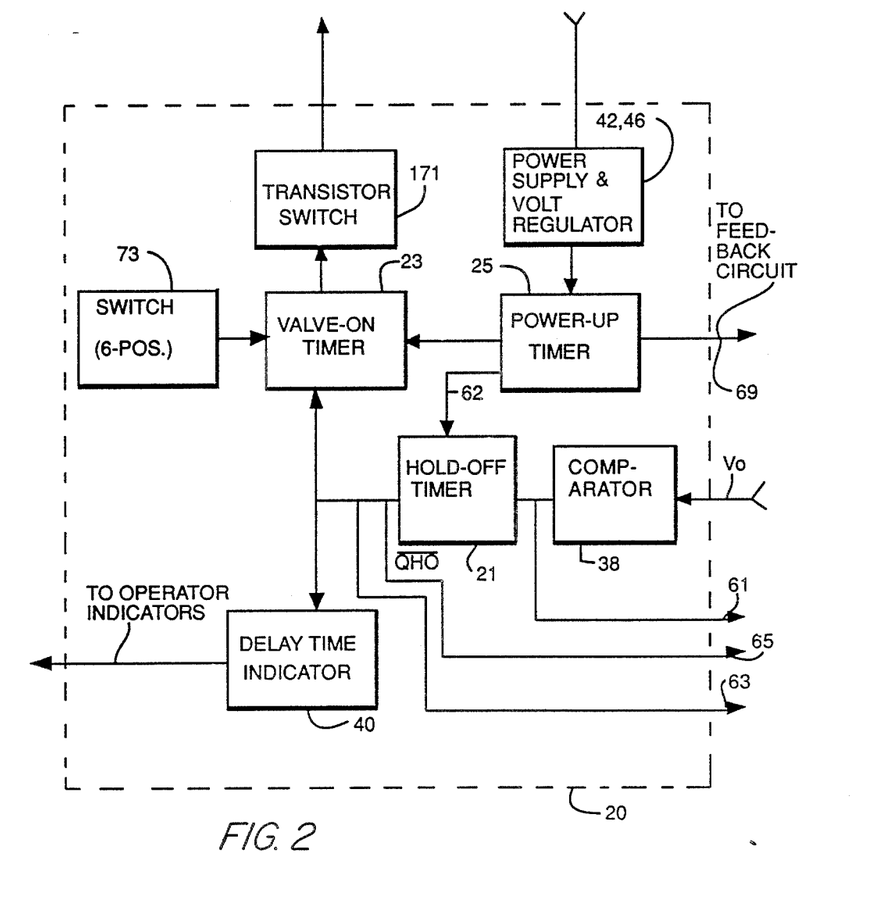
FIG. 2 shows a block diagram of the components comprising the control signal generator module of the oxygen control device.

The hold-off timer is reset upon "power-up" by a power reset pulse received as input at 62 (FIG. 2) from a power-up timer (or reset) circuit 25, in which low-power CMOS circuitry is used to reduce battery current drain. Since it is possible for the hold-off timer to cause a power-supply surge which could disturb the more sensitive sensor bridge and amplifier circuit, hold-off timer 21 is powered by the unregulated supply 67 (6V), rather than the regulated supply 68 (4.8V), as supply regulation is not important to the hold-off timer circuit.

Valve-On Timer 23

The front edge of the output pulse produced by the hold-off timer triggers a valve-on timer. The output from the hold-off timer is actually taken at an inverted output terminal, and therefore it is actually the falling edge of the inverted output that triggers the valve-on timer 23. The other half of an integrated chip IC4538 (used for the hold-off timer), is used for the valve-on timer 23 circuit in the preferred embodiment. The triggering of the valve-on timer produces an output signal delivered to a transistor switch 171 through a base current limiting resistor (not shown) so that when the valve-on timer is "on", the transistor switch is "on". The collector of the transistor is connected as output to solenoid valve 18 and to a 6-volt battery supply. A diode (not shown) is used to prevent damage to the transistor by limiting the inductive surge voltage of solenoid valve 18 which occurs when the transistor switch is turned off. Rapid or multiple pulsing of the solenoid valve is prevented by having valve-on timer 23 be triggered by hold-off timer 21, rather than being triggered directly by the trigger pulse of comparator 38.

The valve-on timer 23 is user adjustable by a 6-position switch 73 which provides for selection of variable widths in the output pulse, and hence variable time periods for oxygen to flow through flow valve 18. In the preferred embodiment, the switch selects from 5 resistors, with typical time intervals being 100, 200, 300, 400 and 500 ms, respectively. A trim capacitor (not shown) in parallel with a primary capacitor (not shown) results in a timing accuracy of about 5%. While the use of 1% tolerance series resistors (not shown) provides an adequately precise ratio of times, the manufacturing tolerances of the timer integrated circuit IC4538 and the main capacitor require that a trim capacitor, with typical values of 0.0047 to 0.047 ufd and a component tolerance of from ±3% to ±5%, also be used in order to achieve the desired precision in the valve-on timer interval.

Power-Up Timer 25

The power-up timer 25 is also one-half of the circuit of an integrated chip IC4538, and is used to produce a pulse about 200 ms wide just after power to the unit is turned on. This pulse resets valve-on timer 23 and hold-off timer 21. A capacitor-resistor combination (not shown) determines the delay (in milliseconds) before the pulse is triggered after the power is turned on and the pulse width is determined also by the product of a capacitor-resistor circuit.

Delay Time Indicator 40

Delay time indicator 40 provides detection of breathing cessation (apnea) by detecting the cessation of trigger signals. Indicator circuit 40 can comprise one-half of integrated chip IC4538, configured as a missing pulse detector. Detection time is user adjustable from 6 to over 60 seconds by a time constant controlled by a variable resistor. A 30 second time constant, or preset time interval, is typical.

The delay time indicator 40 receives as input the output signal of hold-off timer 21. Being a missing pulse detector, circuit 40 is basically the same as a retriggerable timer, since a series of closely-spaced pulses from the hold-off timer will continually trigger circuit 40, keeping its output high. When the pulses stop, i.e., timeout occurs, a transistor switch (not shown) is switched on through a base resistor (not shown) to turn on an LED (not shown). At the same time, a delay timer output signal is generated and delivered from delay time indicator 40 to valve-on timer 23, to cause a control signal to be delivered to flow valve 18 which activates the flow valve causing a pulse of oxygen to flow. This oxygen pulse oftentimes has the effect of, for example, clearing up a blockage, e.g. mucus, in the cannula 24 or other conduit in the oxygen delivering system.

In the preferred embodiment, an audible buzzer (not shown) is also activated by means of a tone generator (not shown) at a frequency of about 2-3 KHz and an intensity of 80 to 95 dB. Resumption of inhalation by the patient turns off the tone generator and the LED. In the power-up reset phase, the audible alarm and LED are turned off by triggering this timer.

Voltage Regulator 42

Voltage delivered to pressure sensor 30 and to the analog sections of the signal processing circuitry is regulated by means of the low power voltage regulator 42 (FIG. 1). Voltage regulators of this type are presently available, with the integrated circuit ICL7663 used as the voltage regulator in the preferred embodiment. The control voltage is established by means of a voltage divider consisting of a potentiometer (not shown) and fixed resistors (not shown), with a capacitor (not shown) on the output for the filtering of voltage surges. A diode (not shown) is connected in reverse bias across the supply input to protect the circuit in case of polarity (battery) reversal.

In the preferred embodiment, the oxygen delivery device is powered by a external 6-volt battery 46 (5 NiCd cells) which provides the voltage to the voltage regulator, and thus both regulated and unregulated power supply outputs are provided. A battery charger (not shown) allows the nickel-cadmium batteries to be re-used for portable operation. Peak current draw from the battery is less than 100 mA, and is only 2 mA with no solenoid valve, LED or tone generator activated. A 1 amp fuse (not shown) protects the circuit and battery.

Turning now to a typical operation of the control device in accordance with a preferred embodiment of an invention, input port 16 of the three-way solenoid valve 18 is connected to the pressure regulated oxygen supply 12, such as a bottled tank of pressurized oxygen, and, in a first state of value 18, output line or cannula 24 of the solenoid valve 18 provides delivery of oxygen to the patient. As mentioned above, with valve 18 in a second state, the cannula 24 monitors the breathing of the patient and transmits pressure variations to electronic control unit 10 of the invention and, in particular, to pressure sensor 30. More specifically, line 26 of solenoid valve 18 is connected to the input of the pressure sensor 30 and provides a connection to line 24 in the second state of valve 18. Solenoid valve 18 comprises a coil which is connected to receive output signals from control signal generator 20 of the electronic control unit for control of the opening and closing of valve 18.

When there is no inhalation by the patient, i.e., no pressure variation is measured by pressure sensor 30, no signal is outputted from control signal generator 20, so solenoid valve 18 stays closed and no oxygen flows to the patient. The feedback module 36 is switched in as a feedback loop by switch $S_a$ and provides automatic signal correction to the amplified pressure sensor signal, $V_o$.

Upon inhalation by the patient, a pressure change is transmitted through cannula 24 and solenoid valve 18, through line 26 to pressure sensor 30. This causes an output signal to be generated from pressure sensor 30 which is amplified by amplifier 34. Comparator 38 (FIG. 2) receives an amplified and error compensated pressure sensor signal, and compares this signal with a threshold signal, $V_{th}$. When the threshold level is exceeded, a comparator output trigger pulse is generated, such as that shown in FIG. 8(a).

The comparator trigger pulse is inputted to hold-off timer 21 which outputs a 1.5 second pulse output signal in response thereto. The pulse output signal is delivered as input to both valve-on timer 23 and to delay time indicator 40. It activates valve-on timer 23 to generate output control signals having characteristics, such as an adjustable pulse width, based upon the setting of adjustable switch 73, to control the opening and closing of the solenoid valve to activate a flow of oxygen. The leading edge of the control signal inputted to the solenoid valve activates the oxygen flow commencing with the start of inhalation by the patient. The duration of that oxygen flow is, in a preferred embodiment, equal to the time period of the width of the pulsed control signal, which is user adjustable as discussed above, by switch 73.

The same signal that activates valve-on timer 23 is also inputted to Delay Time Indicator 40 which operates as a retriggerable monostable multivibrator to monitor the continued breathing of the patient by detecting a continuous output of hold-off timer circuit pulses within a preset time period. In the event that the comparator signal stops outputting its trigger signal, and hence the hold-off timer circuit is not activated to output its pulsed signal, i.e. patient inhalation has ceased, the delay time indicator circuit generates an alarm signal for alerting the operator of a cessation in patient inhalation. Various types of indicators, such as audio and/or visual alarms can be connected to be activated by the Delay Time Indicator's alarm signal.

Another output from Control Signal Generator 20 controls analog switch $S_a$ to disconnect the automatic zeroing circuit of feedback module 36 during time that solenoid valve 18 is open, and for approximately, 0.5 seconds thereafter. After the latter period passes, i.e., approximately 0.5 second after the valve 18 closes, feedback module 36 is reconnected into the system as a negative, integral feedback loop, to provide signal offset and temperature drift correction. During the remaining portion of the breathing cycle (exhalation, pause) the output from amplifier 3 is higher than the comparator reference threshold level and therefore no trigger pulse is generated by comparator 38 to initiate any further output signal to solenoid valve 18 which, therefore, remains in its normally closed (no oxygen flow) state. Again, if there are no subsequent inhalations within a preset period, an alarm signal is generated by delay time indicator 40 to alert the operator that patient inhalation has ceased.

It will be understood by those skilled in this art that although the invention has been described in relation to exemplary preferred embodiments thereof, variations and modifications can be effected in these preferred embodiments without detracting from the scope and spirit of the invention.

We claim:

1. A flow control device for controlling the flow of oxygen to a patient, said device comprising:
    (a) flow valve means for controlling the amount of oxygen flowing from an oxygen supply to a patient; and
    (b) electronic control means comprising (i) pressure sensor means for sensing pressure changes in the breathing of the patient and for producing sensor output signals in accordance therewith, (ii) feedback means for feeding back said sensor output signals to the pressure sensor means to provide automatic correction of said sensor output signals, the feedback means comprising switch means for automatically disconnecting said feedback means as a function of the sensor output signals, and (iii) control signal generation means connected to said pressure sensor means for producing control signals based on said sensor output signals and for applying said control signals to said flow valve mean to control the flow of oxygen to the patient.

2. A flow control device according to claim 1, wherein said pressure sensor means comprises amplifier means connected to a sensor output for producing an amplified output signal.

3. A flow control device according to claim 2, wherein the control signal generation means comprises comparing means for receiving the amplified output signal and comparing said output signal with a variable threshold level to selectively output a comparator trigger signal for generating said control signals.

4. A flow control device according to claim 3, wherein said feedback means comprises integrator means having a time constant of at least 5 seconds duration and means for feedback signal inversion, connected in series with the switch means, for providing a negative integral feedback signal to the amplifier means.

5. A flow control device according to claim 4, wherein said switch means comprises a first switch position and a second switch position for disconnecting the feedback means from the pressure sensor means at predetermined times.

6. A flow control device according to claim 5, wherein said switch means disconnects the feedback means from the pressure sensor means when oxygen flows through the flow valve means, and connects the feedback means to the pressure sensor means at least a part of the time when oxygen does not flow through the flow valve means.

7. A flow control device according to claim 6, wherein said switch means disconnects the feedback means from the pressure sensor means when oxygen flows through the flow valve means and for approximately 0.5 seconds thereafter, and connects the feedback means to the pressure sensor means at all other times.

8. A flow control device according to claim 5, wherein said feedback means comprises a first correction circuit means for counterbalancing the effect of the integrator means not being connected when said feedback means is disconnected, said first correction circuit means providing a first voltage drop within said feedback means when said feedback means is disconnected so to increase the average value of said amplified output signal.

9. A flow control device according to claim 8, wherein said first correction circuit means comprises a series connection of a first resistor for receiving the amplified output signal, a first diode, and a second resistor, with said first voltage drop occurring at a junction of said first resistor and said first diode.

10. A flow control device according to claim 9, wherein said feedback means comprises a second correction circuit means for increasing the rat at which said amplified output signal shifts back above said threshold level, said second correction circuit being activated to provide a second voltage drop within said feedback means only when the amplified output signal is less than said threshold level for a predetermined time period after oxygen has ceased to be delivered through said flow valve means.

11. A flow control device according to claim 10, wherein said second correction circuit means comprises components that include a capacitor for setting said predetermined time period, a third resistor, a transistor and second and third diodes, whereby all of said components have a common point of connection, said third resistor and said second diode are connected in parallel, and said second voltage drop is produced at said junction of the first resistor and the first diode.

12. A flow control device according to claim 9, wherein said control signal generation means comprises hold-off timer means for receiving said comparator trigger signal and outputting a hold-off pulse of predetermined width, valve-on timer means for receiving the hold-off pulse and for generating a valve-on signal in response thereto for producing said control signals.

13. A flow control device according to claim 12, wherein said electronic control means comprises a delay time indicator connected to receive the hold-off pulse for measuring time between patient inhalations, and for generating an alarm signal when a predetermined time passes without detection of patient inhalation.

14. A flow control device according to claim 13, wherein said alarm signal is inputted to said flow valve means to actuate a flow of oxygen to the patient.

15. A flow control device according to claim 13, wherein said delay time indicator comprises an adjustable timer and indicator means for alerting an operator when said alarm signal is generated.

16. A flow control device according to claim 13, wherein said detection of patient inhalation is determined by receipt of pulses outputted from said hold-off timer means.

17. A flow control device according to claim 13, wherein said predetermined time is user adjustable from approximately 6 to 60 seconds by a time constant circuit comprising a variable resistor.

18. A flow control device according to claim 13, wherein the delay time indicator comprises a transistor switch for generating said alarm signal, and deactivation means for automatically terminating said alarm signal when inhalation is resumed.

19. A flow control device according to claim 12, wherein the valve-on timer means comprises transistor switch means having a transistor base limiting resistor connected to receive the valve-on signal, and a transistor collector as an output terminal for connection of said control signals to said flow valve means.

20. A flow control device according to claim 12, wherein said control signal generation means comprises power-up timer means for generating a reset pulse when power is activated to the flow control device, said reset pulse being inputted to said hold-off timer means, to said valve-on timer means and to said feedback means for resetting the hold-off and the valve-on timer means, and for establishing a fast zero in said integrator means.

21. A flow control device according to claim 20, wherein said integrator means comprises zeroing means for receiving said reset pulse and changing said integrator time constant to a value less than 0.5 seconds for quickly establishing a zero reference within said integrator means.

22. A flow control device according to claim 20, wherein the reset pulse has a pulse width determined by a capacitor-resistor circuit.

23. A flow control device according to claim 22, wherein a delay occurs before output of said reset pulse after said power is activated, the time of the delay being adjustably determined by a capacitor-resistor combination.

24. A flow control device according to claim 12, wherein the predetermined width of the hold-off pulse is determined by a resistor-capacitor circuit for blocking an output of other signals from said hold-off timer means while said hold-off pulse is being outputted.

25. A flow control device according to claim 24, wherein said hold-off pulse has a pulse width of approximately 1.5 seconds.

26. A flow control device according to claim 12, wherein the valve-on timer means is triggered by an inverted front edge of said hold-off pulse.

27. A flow control device according to claim 1, wherein said flow valve means comprises a solenoid valve having an input terminal for receiving said control signal for opening and closing said solenoid valve, a first valve port for receiving a regulated oxygen supply through an orifice, a second valve port for outputting oxygen to a patient, and transfer means for receiving pressure variations from the patient and delivering said pressure variations to said pressure sensor means.

28. A flow control device according to claim 27, wherein said transfer means is deactivated during the time that oxygen flows through the solenoid valve to the patient.

29. A flow control device according to claim 12, wherein the valve-on timer means comprises adjustable switch means for varying a pulse width of said control signals to select a time interval of oxygen flow.

30. A flow control device according to claim 29, wherein said adjustable switch means comprises a six position switch for varying the control signal pulse width to produce time intervals of oxygen flow from 100 ms to 500 ms in equal switch position increments.

31. A flow control device according to claim 12, wherein said hold-off timer means comprises a hold-off first output for output of said hold-off pulse, and a hold-off second output for concurrent output of an inverted hold-off pulse, with said second output connected as input to said first correction circuit for activation of said first correction circuit during the input of the inverted hold-off pulse.

* * * * *